United States Patent [19]

Govier

[11] Patent Number: 4,900,541

[45] Date of Patent: Feb. 13, 1990

[54] SUNSCREEN COMPOSITION

[76] Inventor: William C. Govier, 16575 Park Lane Dr., Los Angeles, Calif. 90049

[21] Appl. No.: 191,192

[22] Filed: May 6, 1988

[51] Int. Cl.[4] .................... A61K 7/021; A61K 7/40; A61K 9/12; A61K 35/14

[52] U.S. Cl. ..................... 424/47; 252/106; 252/312; 424/59; 424/60; 424/63; 424/64; 424/73; 424/101; 514/873; 514/937; 514/938

[58] Field of Search ............. 424/59, 101, 47

[56] References Cited

FOREIGN PATENT DOCUMENTS

WO86/3122  6/1986  PCT Int'l Appl. .

OTHER PUBLICATIONS

Knighton et al., "Role of Platelets and Fibrin in the Healing Sequence", *Annals of Surgery,* 196, 379–388 (1982).

Knighton et al., "Classification and Treatment of Chronic Nonhealing Wounds", *Annals of Surgery,* 204, 322–330 (1986).

*Primary Examiner*—Dale R. Ore

[57] ABSTRACT

A skin care composition which contains platelet derived growth factors is provided. Such a composition in the form of a shave cream or foam, after shave lotion, moisturizing cream, sun tan lotion, lipstick, etc. assists in restoring the skin to its natural condition when the skin is damaged by cuts, abrasions, sun, wind, and the like.

3 Claims, No Drawings

SUNSCREEN COMPOSITION

FIELD OF INVENTION

This invention relates to skin care compositions and treatments which contain activated platelet factors, more particularly to such compositions and treatments which contain platelet derived growth factor.

BACKGROUND OF THE INVENTION

A broad range of liquids, creams, lotions, emulsions, oils, gels, etc. have been used for topical application to the skin to protect the skin from various elements or conditions such as the sun, wind, cold and dryness or to treat the skin after it has been subjected to such elements or conditions, or after it has been cut or abraded. These products covering a wide range of cosmetics are generally used to help maintain the skin in its normal condition, to aid in restoring it to its normal condition, or to improve the visual appearance of the skin. The skin conditions addressed by cosmetics and treatment compositions are too numerous to mention.

Activated platelet factors such as platelet derived growth factor have been shown to be useful wound healing substances. Knighton in International Patent Publication Number WO 86/03122 teaches the preparation of platelet-drived growth factor (PDGF) and platelet-derived angiogenesis factor (ADAF) by the activation of platelet-rich plasma from whole blood with thrombin. These activated factors are then applied to a non-healing wound in a medicated salve.

Knighton et al. in "Role of Platelets and Fibrin in the Healing Sequence," Annals of Surgery, 196, 379–388 (1982) describe the successful treatment of a non-healing wound in patient upon the administration of a ten-unit platelet transfusion. As the title of the article suggests, the role of platelets in the wound healing is described.

Knighton et al. in "Classification and Treatment of Chronic Nonhealing Wounds," Annals of Surgery, 204, 322–320 (1986) describe the successful treatment of wounds in patients using platelet-derived wound healing factors (PDWHF) obtained from each patient's blood.

SUMMARY OF THE INVENTION

According to the present invention there is provided a skin care composition comprising at least one activated platelet factor as an ingredient in a cosmetically acceptable carrier.

Further provided is a method of treating skin in order to assist and promote its natural healing and repair process comprising: applying to the area of the skin to be treated an effective amount of at least one activated platelet factor in a cosmetically acceptable carrier.

DETAILED DESCRIPTION OF THE INVENTION

The cosmetic compositions of this invention can be any of the creams, lotions, liquids, emulsions, oils, films, soaps, lipsticks, pastes, foams, mousses, etc. known to those in the cosmetic arts. The ingredients of these compositions are combined using known cosmetic product techniques. Those skilled in the art will be fully aware of the carriers and other ingredients which go into making the various cosmetic product forms.

Activated platelet factors which can be used as ingredients in cosmetic products are those released from animal or human blood by thrombin or another activating agent such as ultrasound. Preferred activated platelet factors are PDGF and PDAG prepared from blood as described by Knighton in WO 86/03122. While human blood can be used as the source of these factors, it is preferred to obtain them from animal blood (cows and horses, for example) for economic reasons. Any activated platelet factor used must be sterilized using known techniques to remove any viral or bacterial contaminants which may be in the blood.

Platelet derived growth factors are used in the cosmetic products in amounts effective to assist in restoring the skin to its natural condition after it has been damaged by various conditions. In general, the cosmetic products will contain about 0.01 to 10 parts by weight of activated platelet factor per 100 parts by weight of the total composition. The factor content may be higher or lower than that specified depending upon the cosmetic product used and the skin condition to be treated. For example, an after-shave lotion, shaving cream, or stip-stick may contain a higher factor content to treat shaving cuts and abrasions than a skin moisturizing lotion.

The cosmetic compositions of the invention is whatsoever form used assists the natural healing processes of the skin when it is damaged by cuts, abrasions, sun, wind, pollutants and the like. Such skin damage can occur through shaving, falls, and accidents; or through climatic and environmental skin irritants, such as dry winds, winter cold, chemicals, detergents, and other household cleaners and air pollution.

Examples of cosmetic formulations of the present invention are shown below, it being understood that these examples are by way of illustration and not limitation.

EXAMPLE 1

| Sun-tan Oil | |
|---|---|
| | Percent |
| Sesame oil | 24.0 |
| PDGF | 2.0 |
| Mineral oil | 50.0 |
| Isopropyl myristate | 24.0 |
| Sun-screen | q.s. |
| Perfume | q.s. |
| Antioxidant | q.s. |
| Color | q.s. |

EXAMPLE 2

| Non-greasy sun-tan cream | |
|---|---|
| | Percent |
| Stearic acid | 15.0 |
| PDGF | 1.0 |
| Potassium hydroxide | 0.5 |
| Sodium hydroxide | 0.18 |
| Cetyl alcohol | 0.5 |
| Lanolin | 2.0 |
| Glycerin | 5.0 |
| Water | 75.82 |
| Sun-screen | q.s. |
| Preservative | q.s. |
| Perfume | q.s. |

EXAMPLE 3

| Lipstick, Chapstick | |
|---|---|
| | Percent |
| Beeswax | 10.0 |
| Ozokerite | 24.0 |
| Carnauba wax | 8.0 |
| Paraffin wax | 8.0 |
| Lanolin | 10.0 |
| Liquid paraffin | 22.0 |
| Eosin solvent | 8.0 |
| Bromo acid | 2.5 |
| Modifying lakes, colors | 6.0 |
| Flavor | 1.4 |
| PDGF | 0.1 |

EXAMPLE 4

| Shaving cream (for aerosol or non-aerosol) | |
|---|---|
| | Percent |
| Stearic acid | 16.0 |
| PDGF | 5.0 |
| White mineral oil | 4.0 |
| Lanolin | 3.5 |
| Terpineol | 0.1 |
| Polyethylene glycol 600 monostearate | 3.2 |
| Potassium hydroxide | 0.8 |
| Propylene glycol | 4.0 |
| Water | 63.4 |

EXAMPLE 5

| Body/Hand Lotion | |
|---|---|
| | Percent |
| Cetyl alcohol | 0.5 |
| Lanolin | 1.0 |
| Petroleum | 14.0 |
| Stearic acid | 4.0 |
| Isopropanolamines | 0.8 |
| Glycerin | 5.0 |
| Methyl p-hydroxybenzoate | 0.2 |
| Titanium dioxide | 0.1 |
| Water | 64.4 |
| PDGF | 10.0 |

EXAMPLE 6

| Foundation cream | |
|---|---|
| | Percent |
| Stearic acid | 18.0 |
| PDGF | 5.0 |
| Potassium hydroxide | 0.52 |
| Sodium hydroxide | 0.18 |
| Cetyl alcohol | 0.50 |
| Glycerin | 18.0 |
| Preservative | q.s. |
| Water | 57.2 |
| Perfume | 0.6 |

EXAMPLE 7

| Liquid foundation cream | |
|---|---|
| | Percent |
| Mineral oil | 30.0 |
| PDGF | 3.0 |
| Lanolin | 8.0 |
| Microcrystalline wax | 1.0 |
| Arlacel 83 | 2.3 |
| Tween 60 | 0.1 |
| Powder base | 8.0 |
| Glycerol | 5.0 |
| Water | 42.6 |
| Perfume | q.s. |
| Preservative | q.s. |

EXAMPLE 8

| Vanishing cream | |
|---|---|
| | Percent |
| Stearic acid | 15.0 |
| PDGF | 0.01 |
| Potassium hydroxide | 0.5 |
| Sodium hydroxide | 0.18 |
| Cetyl alcohol | 0.5 |
| Isopropyl myristate | 3.0 |
| Glycerin | 5.0 |
| Water | 75.81 |
| Preservative | q.s. |
| Perfume | q.s. |

What is claimed is:

1. A sun screen composition comprising an effective amount of at least one activated platelet factor and at least one sun screen agent in a cosmetically acceptable carrier in the form of a cream, lotion, emulsion, oil or film, foam, or mousse.

2. A skin care composition of claim 1 wherein the activated platelet factor is platelet derived growth factor.

3. A skin composition of claim 2 containing about 0.01 to 10 parts by weight of platelet derived growth factor per 100 parts by weight of the total composition.

* * * * *